United States Patent
Ito

(10) Patent No.: US 7,780,326 B2
(45) Date of Patent: Aug. 24, 2010

(54) OPTICAL FIBER LIGHTING APPARATUS

(75) Inventor: Takeshi Ito, Hino (JP)

(73) Assignee: Olympus Corporation, Tokyo (JP)

( * ) Notice: Subject to any disclaimer, the term of this patent is extended or adjusted under 35 U.S.C. 154(b) by 198 days.

(21) Appl. No.: 12/186,903

(22) Filed: Aug. 6, 2008

(65) Prior Publication Data
US 2009/0040781 A1 Feb. 12, 2009

(30) Foreign Application Priority Data
Aug. 10, 2007 (JP) ............... 2007-210035

(51) Int. Cl.
*F21V 7/04* (2006.01)
(52) U.S. Cl. .................. 362/554; 362/553; 362/555
(58) Field of Classification Search .......... 362/553, 362/554, 555, 574
See application file for complete search history.

(56) References Cited
U.S. PATENT DOCUMENTS
6,843,590 B2 * 1/2005 Jones et al. ............ 362/554

2007/0103925 A1 * 5/2007 Henson et al. .......... 362/554
2010/0080016 A1 * 4/2010 Fukui et al. ............ 362/574

FOREIGN PATENT DOCUMENTS
JP 2006-314686 11/2006

* cited by examiner

*Primary Examiner*—David V Bruce
(74) *Attorney, Agent, or Firm*—Scully, Scott, Murphy & Presser, P.C.

(57) ABSTRACT

An optical fiber lighting apparatus includes an exciting light source, a first optical fiber, a second optical fiber, and a wavelength conversion unit. The first optical fiber guides the exciting light emitted from the exciting light source. The wavelength conversion unit receives the exciting light exiting from the first optical fiber to generate a wavelength-converted light having a wavelength different from that of the exciting light. The second optical fiber guides at least part of the wavelength-converted light generated by the wavelength conversion unit.

9 Claims, 5 Drawing Sheets

US 7,780,326 B2

OPTICAL FIBER LIGHTING APPARATUS

CROSS-REFERENCE TO RELATED APPLICATIONS

This application is based upon and claims the benefit of priority from prior Japanese Patent Application No. 2007-210035, filed Aug. 10, 2007, the entire contents of which are incorporated herein by reference.

BACKGROUND OF THE INVENTION

1. Field of the Invention

The present invention relates to an optical fiber lighting apparatus.

2. Description of the Related Art

There has been proposed an optical fiber lighting apparatus that has LEDs arranged at the proximal end portion of an endoscope and guides light to the light-emitting unit at the distal end of the endoscope via an insertion portion by using a fiber bundle. The fiber bundle is a single bundle on the endoscope distal end side but is separated into three parts on the light source side, which are respectively and optically connected to the LEDs that emit red light, green light, and blue light.

This optical fiber lighting apparatus guides illumination light from the endoscope proximal end portion to the endoscope distal end portion by using the fiber bundle. Since the light guide efficiency of an optical fiber generally depends on the wavelength, the RGB output ratio at the incident end and that at the exit end are different depending on the length of the fiber bundle. In order to obtain a desired RGB output ratio at the exit end, the RGB output ratio at the incident end has to be adjusted in accordance with the length of the fiber bundle.

BRIEF SUMMARY OF THE INVENTION

An object of the present invention is to provide an optical fiber lighting apparatus suitable for use in an endoscope.

An optical fiber lighting apparatus according to the present invention: an exciting light source that emits exciting light; a first optical fiber that guides the exciting light emitted from the exciting light source; a wavelength conversion unit that receives the exciting light exiting from the first optical fiber to generate wavelength converted light having a wavelength different from that of the exciting light; and a second optical fiber that guides at least part of the wavelength converted light generated by the wavelength conversion unit.

Advantages of the invention will be set forth in the description that follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

The embodiments of the present invention will be described below with reference to the views of the accompanying drawing.

First Embodiment

Figure 1:
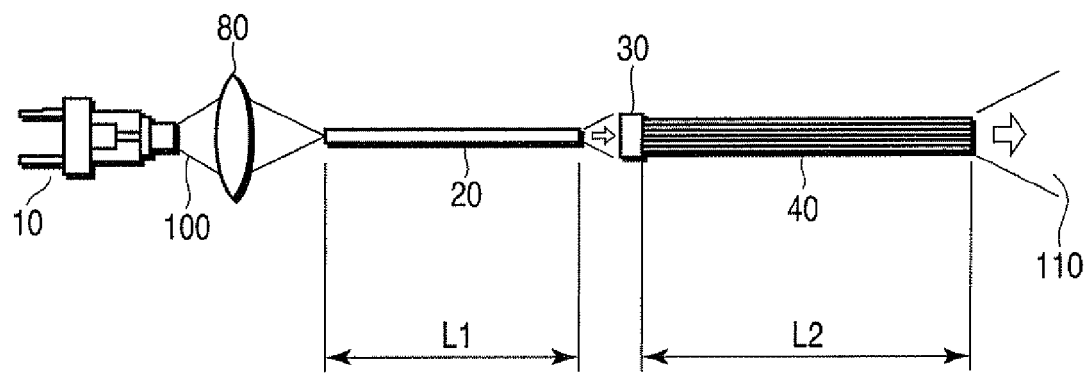
FIG. 1 is a schematic view of an optical fiber lighting apparatus according to the first embodiment of the present invention.

FIG. 1 shows an optical fiber lighting apparatus according to the first embodiment of the present invention. As shown in FIG. 1, the optical fiber lighting apparatus includes a semiconductor laser 10 that emits laser light and serves as an exciting light source for emitting exciting light 100, a single fiber 20 as the first optical fiber that guides the exciting light 100 exiting from the semiconductor laser 10, a phosphor unit 30 as a wavelength conversion unit that receives the exciting light 100 emitted from the single fiber 20 to generate fluorescence as wavelength-converted light having a wavelength different from the exciting light 100, and a fiber bundle 40 including a plurality of single fibers as the second optical fiber that guides at least part of the wavelength-converted light, i.e., the fluorescence, generated from the phosphor unit 30. A condenser lens 80 is placed between the semiconductor laser 10 and the single fiber 20. The condenser lens 80 focuses the exciting light 100 emitted from the semiconductor laser 10 onto the incident region of the single fiber 20.

Referring to FIG. 1, the exciting light 100 emitted from the semiconductor laser 10 is focused by the condenser lens 80 and strikes the single fiber 20. The exciting light 100 striking the single fiber 20 is guided by the single fiber 20 and exits from the exit end of the single fiber 20. The exciting light 100 exiting from the single fiber 20 strikes the phosphor unit 30. Part of the exciting light 100 enters the phosphor unit 30 and is converted into fluorescence having a longer wavelength than the exciting light 100 by the phosphor in the phosphor unit 30. Part of the fluorescence and part of the exciting light 100 strike the fiber bundle 40 and exits as illumination light 110 from the exit end of the fiber bundle 40.

When this optical fiber lighting apparatus is used for an endoscope, the length of the single fiber 20 can be arbitrarily selected as needed. However, the length of the fiber bundle 40 needs to be selected in consideration of the generation of heat at the distal end portion of the endoscope and the like. That is, when a brightness corresponding to approximately 20 lm is achieved, the temperature of the phosphor unit 30 rises by approximately 40° C. due to heat generation relative to the ambient temperature without any heat dissipation mechanism. For this reason, it is necessary to determine the length of the fiber bundle 40 in consideration of the arrangement of the peripheral part of the phosphor unit 30, the influence of heat on the outside of the unit, and the like. In consideration of the influences of heat on devices provided in an image sensing device integrated in the distal end portion of the endoscope and the human body as an observation target, the phosphor unit 30 needs to be spaced apart from the distal end of the insertion portion of the endoscope by 10 cm or more. That is, the fiber bundle 40 preferably has a length of 10 cm or more. This can reduce the generation of heat from the distal end portion of the endoscope.

Figure 2:
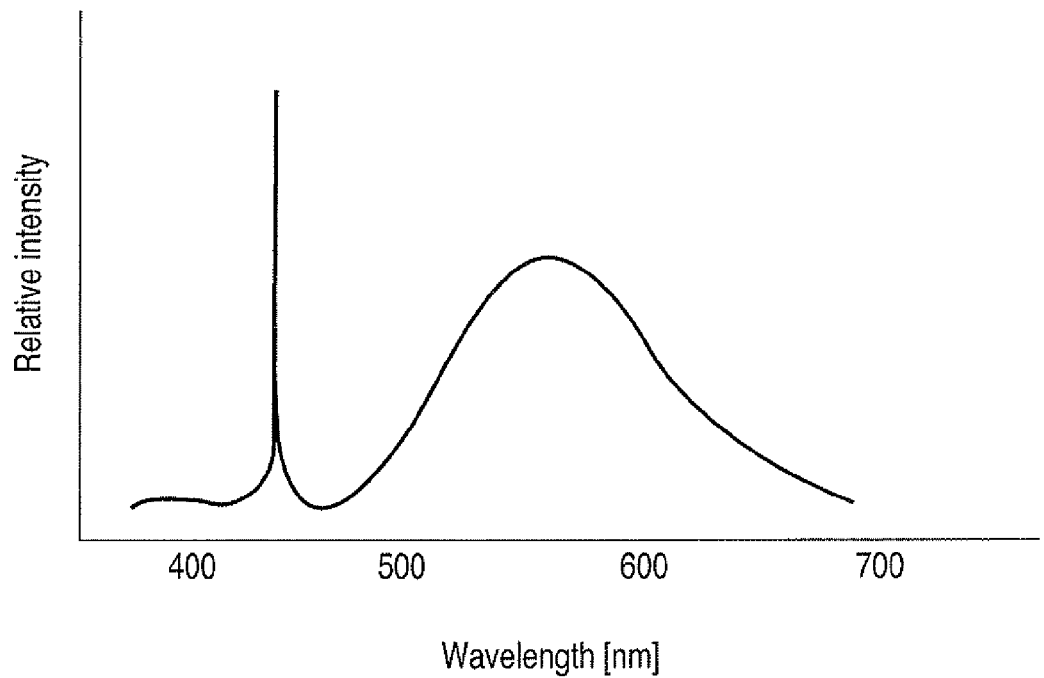
FIG. 2 is a graph showing the spectrum of illumination light exiting from the optical fiber lighting apparatus in FIG. 1.

The semiconductor laser 10 is a blue semiconductor laser source having a peak at a wavelength of 480 nm or less. For example, this laser is a blue semiconductor laser that emits light in the 440-nm blue band. The phosphor unit 30 contains a phosphor that generates fluorescence having a peak at least 540 nm or more. This phosphor is, for example, a cerium-doped YAG phosphor that generates light with a spectrum having a peak at 560 nm and spreading to a wavelength range of 700 nm or more. FIG. 2 shows the spectrum of the illumination light 110 exiting from the fiber bundle 40. In the case of white light having such a spectrum, only laser light of almost 440 nm is a blue component, and hence the light guide loss of blue light can be represented by the light guide loss of the peak value at 440 nm.

Figure 3:
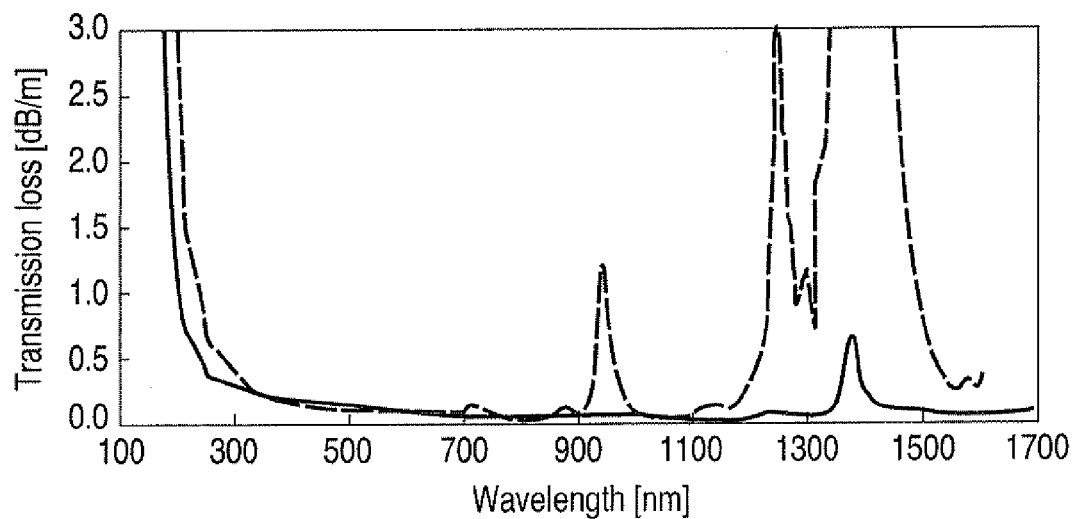
FIG. 3 is a graph showing the transmission loss characteristic of a general optical fiber for guiding light in the visible light range.

Both the single fiber 20 and the fiber bundle 40 are general optical fibers for guiding light in the visible light range, and have a transmission loss characteristic like that shown in FIG. 3. Referring to FIG. 3, the dotted line corresponds to a general optical fiber, and the solid line corresponds to a high-quality optical fiber. As shown in FIG. 3, when the high-quality optical fiber is used, the characteristics in the infrared and ultraviolet ranges improve, but the characteristic in the visible light range is almost similar to that when a general optical fiber is used. As shown in FIG. 3, the transmission losses in the 440-nm band and the 560-nm band are approximately 0.2 dB/m and approximately 0.1 dB/m, respectively, and their difference is only approximately 0.1 dB. This means in terms of transmittance that the light component in the 440-nm band is reduced by 2.3% per meter as compared with the light component in the 560-nm band. When this optical fiber is used, therefore, as the light generated from the phosphor unit is guided, a blue component decreases in accordance with the distance. For this reason, if a length L2 of the fiber bundle 40 is too large, the yellow to red color components of illumination light 110 exiting from the exit end increase. That is, the spectrum of light exiting from the exit end of the fiber bundle 40 decreases in the blue region as compared with a desired RGB output ratio. In other words, the difference between a spectrum pattern corresponding to the desired RGB output ratio and the spectrum pattern of light actually exiting from the optical fiber in the 400 to 500 nm band is larger than a predetermined value as compared with a longer wavelength range.

For this reason, in this embodiment, the length L2 of the fiber bundle 40 is set to 1 m, and the length L1 of the single fiber 20 is set to 3 m. With this setting, the exciting light emitted from the exciting light source strikes the single fiber 20 and is guided by 3 m to be applied to the phosphor unit 30. If the amount of light striking the single fiber 20 is 1, since this optical fiber has a loss of 0.2 dB/m in the 440-nm band, the amount of light decreases to 0.87 when it is applied to the phosphor unit 30. At this point of time, however, since only monochrome light is guided, only a light guide loss occurs, which has no influence on the spectrum of the illumination light 110.

This exciting light is then applied to the phosphor unit 30. The light generated from the phosphor unit 30 has a spectrum like that shown in FIG. 2. The peak intensity of exciting light having a wavelength of 440 nm is adjusted to be slightly higher than that of fluorescence having a wavelength of 560 nm so as to generate white light. In this case, if the peak intensity at each wavelength at the incident end of the fiber bundle 40 is 1, the intensities of 440-nm blue light and 560-nm fluorescence at the exit end become 0.955 and 0.977, respectively, after the light and the fluorescence are transmitted through the fiber bundle 40 by 1 m. The difference between them is therefore approximately 2.2%. According to this embodiment, therefore, when the light source unit that transmits light by 4 m is used, the difference between the intensities of 440-nm light and 560-nm light when light of each color is guided by 4 m as in the prior art, which is 9%, can be reduced to 2.2%. That is, the difference between the spectrum of light exiting from the exit end of the fiber bundle 40 and a spectrum pattern corresponding to a desired RGB output ratio can be made to fall within a predetermined range.

As described above, in this embodiment, the light guided by the fiber bundle 40 is white light and has a wide range of wavelengths, and the length of the fiber bundle 40 is set on the basis of the light guide loss in the wavelength range of light guided by the fiber bundle 40. More specifically, the length of the fiber bundle 40 is selected to 1 m to reduce the difference between waveguide efficiencies of light beams guided by the fiber bundle 40 in the wavelength range to 2.2% or less.

With this arrangement, even if optical fiber lighting apparatuses respectively having lengths of 2 m, 4 m, and 10 m by using identical phosphor units and identical exciting light sources, adjusting the lengths of the single fibers 20 can provide stable optical fiber lighting apparatuses in which the emission spectra of illumination light beams 110 exiting from the exit ends of the fiber bundles 40 remain unchanged. Even if only optical fiber lighting apparatuses having the same length are manufactured, since the spectrum adjusted by the phosphor unit 30 alone does not greatly change, there is no need to perform spectrum evaluation by attaching the second optical fiber. This can reduce the load in the design and manufacture steps. In addition, even if different types of optical fibers are to be used as second optical fibers in accordance with an application, calculating the maximum length of each optical fiber in advance from the light guide loss characteristic of the optical fiber eliminates the necessity to adjust the phosphor unit 30 for each type of optical fiber. Even if only the second optical fiber is replaced, no large change occurs in color appearance.

As described above, according to this embodiment, it is possible to reduce the influence of a change in the length of the fiber bundle 40 on the color appearance of illumination light and provide a stable optical fiber lighting apparatus in which the color appearance in the wavelength range of illumination light does not change.

Second Embodiment

Figure 4:
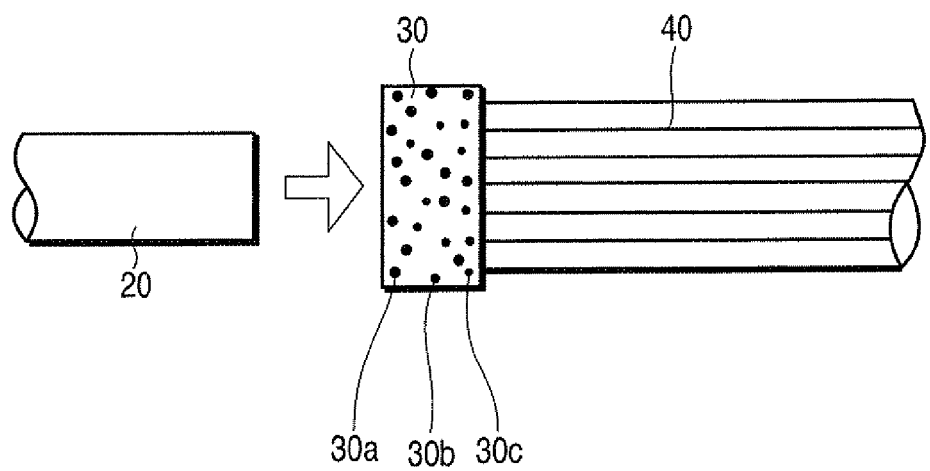
FIG. 4 is a view showing the peripheral part of the phosphor unit of an optical fiber lighting apparatus according to the second embodiment of the present invention.

FIG. 4 shows the peripheral part of the phosphor unit of an optical fiber lighting apparatus according to the second embodiment of the present invention. The optical fiber lighting apparatus of this embodiment has the same basic structure as that of the first embodiment except that a phosphor unit 30 comprises R, G, and B phosphors 30a, 30b, and 30c that respectively generate fluorescences corresponding to red (R), green (G), and blue (B) and are mixed with a resin.

Figure 5:
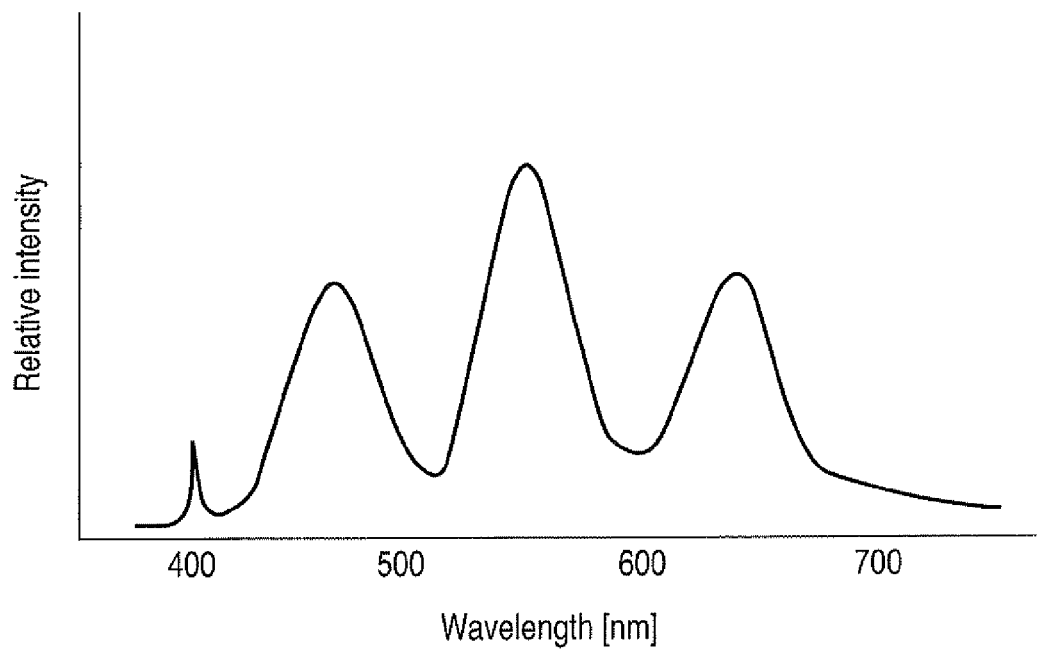
FIG. 5 is a graph showing the spectrum of fluorescence generated from the phosphor unit shown in FIG. 4.

In this embodiment, a semiconductor laser 10 as an exciting light source is a 405-nm violet laser source, and the phosphor unit 30 contains the general R, G, and B phosphors 30a, 30b, and 30c that are excited by light in this wavelength band. The R, G, and B phosphors 30a, 30b, and 30c are excited by 405-nm exciting light to generate 460-nm blue fluorescence, 540-nm green fluorescence, and 630-nm red fluorescence, respectively. FIG. 5 shows the spectrum of fluorescence generated from the phosphor unit 30. As shown in FIG. 5, the 405-nm exciting light is converted into almost R, G, and B fluorescences by the phosphor unit 30, and hence is lower in intensity than the spectrum in the first embodiment shown in FIG. 2. This exciting light has almost no influence on the color appearance of illumination light 110. Consider therefore only the emission of light from the R, G, and B phosphors 30a, 30b, and 30c. As is obvious from FIG. 3, the transmission losses at the respective wavelengths, i.e., 460 nm, 540 nm, and 630 nm, are approximately 0.2 dB/m, 0.1 dB/m, and 0.05 dB/m, respectively. Note that light beams with the respective wavelengths that are generated from the phosphors each have a broader spectrum than exciting light, and there are light beams having wavelengths shorter and longer than the peak wavelength. Light generated from the phosphors has a half-width value of about several ten nm, and a transmission loss can be approximately obtained by using the value of the transmission loss at the peak wavelength. According to this technique, a difference $\Delta\alpha$ between the maximum and minimum values of transmission losses is the difference between the transmission losses at 450 nm and 650 nm, and can be given by $\Delta\alpha=0.15$ dB/m. That is, a shift occurs by 3.4% per meter.

When this light source is to be used, the range of the length of a fiber bundle 40 as the second optical fiber is calculated as 3 m by using $Lmax=\Delta\lambda/((1-10^{(-\Delta\alpha/10)})\times100)$ with an allowable value $\Delta\lambda$ of the difference between intensity changes of the spectra of the respective wavelength components being set to 10%. That is, setting the difference between the maximum and minimum lengths of the second optical fiber to 3 m or less can set $\Delta\lambda$ to 10% or less.

In other words, letting $\Delta\alpha$ [dB/m] be the difference between the maximum and minimum values of light guide losses due to the fiber bundle 40 in the wavelength range of the illumination light 110 exiting from the fiber bundle 40 and $\Delta\lambda$ [%] be the allowable value of the difference between the intensity changes of the spectra of the respective wavelength components in the wavelength range of the illumination light 110, the range of the length of the fiber bundle 40 is preferably equal to or less than $Lmax$ [m]=$\Delta\lambda/((1-10^{(-\Delta\alpha/10)})\times100)$.

The light guided by the fiber bundle 40 has peaks in the intensity spectrum, and the difference $\Delta\alpha$ between the maximum and minimum values of light guide losses is the value obtained by subtracting the minimum value of light guide losses at the wavelengths of peaks from the maximum value of the light guide losses.

The light guided by the fiber bundle 40 has a wide range of wavelengths, and the length of the fiber bundle 40 is determined so that the spectrum of light exiting from the exit end of the fiber bundle 40 has a predetermined pattern corresponding to a desired RGB output ratio at the exit end.

The allowable value $\Delta\lambda$ of the differences between the intensity changes of the spectra of the respective wavelength components varies depending on the application purpose of the lighting apparatus. When the apparatus is to be used for general lighting purposes, the allowable value is preferably approximately 10%. When the apparatus is to be used for medical purposes, the allowable value is preferably approximately 5%. That is, the difference between a spectrum pattern corresponding to a desired RGB output ratio and the spectrum pattern of light exiting from the exit end of the fiber bundle 40 is preferably a predetermined value or less. That is, this allowable range is preferably set to 10% or less for general lighting purposes and to 5% or less for medical purposes. For example, for medical purposes, suppressing the length of the fiber bundle within 1.5 m can implement more desirable illumination light.

According to this embodiment, it is possible to reduce the influence of a change in the length of the fiber bundle 40 on an RGB output ratio and provide a stable optical fiber lighting apparatus in which the color appearance of illumination light does not change in the wavelength range of the illumination light.

Third Embodiment

Figure 6:
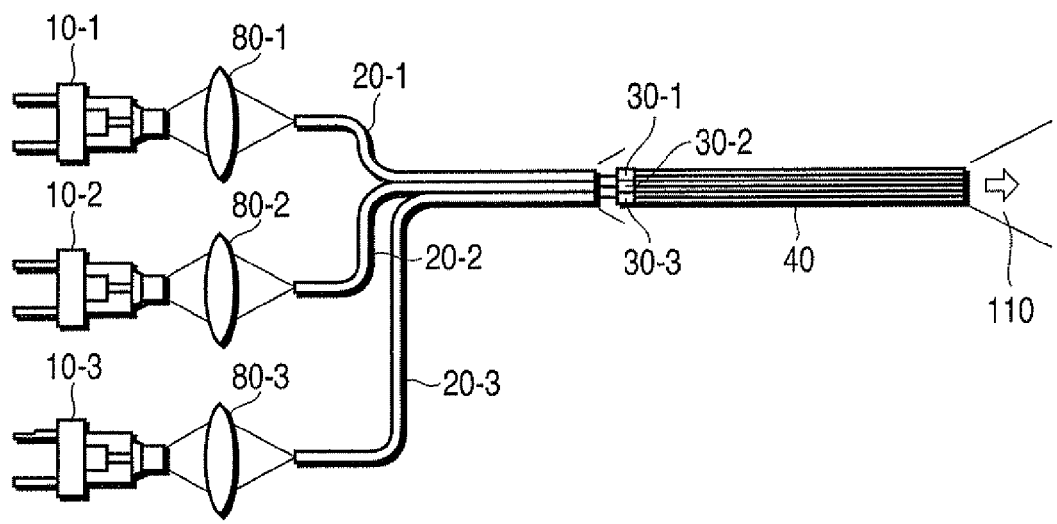
FIG. 6 is a schematic view of an optical fiber lighting apparatus according to the third embodiment of the present invention.

FIG. 6 shows an optical fiber lighting apparatus according to the third embodiment of the present invention. The optical fiber lighting apparatus according to this embodiment has the same basic structure as that of the first embodiment. As shown in FIG. 6, however, this apparatus includes, in place of the semiconductor laser 10, semiconductor lasers 10-1, 10-2, and 10-3 that respectively emit exciting light beams. The apparatus also includes, in place of the single fiber 20, single fibers 20-1, 20-2, and 20-3 that respectively guide exciting light beams emitted from the semiconductor lasers 10-1, 10-2, and 10-3. The apparatus further includes, in place of the phosphor unit 30, phosphor units 30-1, 30-2, and 30-3 that respectively receive the exciting light beams exiting from the single fibers 20-1, 20-2, and 20-3 to generate wavelength-converted light beams having different wavelengths. In addition, condenser lenses 80-1, 80-2, and 80-3 that respectively focus the exciting light beams emitted from the semiconductor lasers 10-1, 10-2, and 10-3 onto the incident regions of the single fibers 20-1, 20-2, and 20-3 are arranged between the semiconductor lasers 10-1, 10-2, and 10-3 and the single fibers 20-1, 20-2, and 20-3 in place of the condenser lens 80.

The phosphor units 30-1, 30-2, and 30-3 respectively contain phosphors that generate fluorescences in the red region of 630 mm, the green region of 540 mm, and the blue region of 460 mm. The wavelengths of light exiting from the semiconductor lasers 10-1, 10-2, and 10-3 are desirably selected in accordance with the exciting efficiencies of these phosphors.

Figure 7:
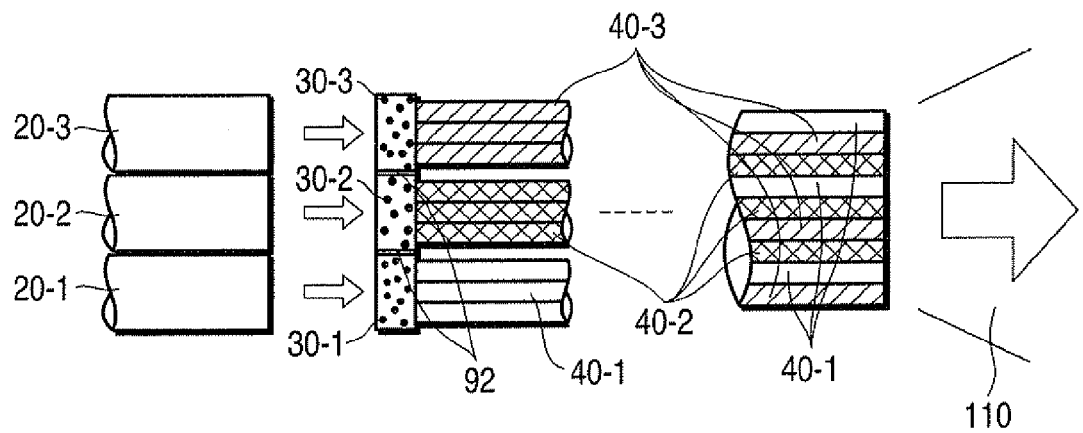
FIG. 7 is an enlarged view of the peripheral part of the phosphor unit of the optical fiber lighting apparatus in FIG. 6.

FIG. 7 is an enlarged view of the peripheral parts of the phosphor units 30-1, 30-2, and 30-3. As shown in FIG. 7, light-shielding members 90 are provided between the phosphor units 30-1, 30-2, and 30-3. A fiber bundle 40 comprises partial fiber bundles 40-1, 40-2, and 40-3 respectively connected to the phosphor units 30-1, 30-2, and 30-3. The arrangement of the single fibers constituting the fiber bundle 40 in the incident end is different from that in the exit end. The single fibers constituting the partial fiber bundles 40-1, 40-2, and 40-3 are arranged so as to be almost uniformly mixed in the exit end of the fiber bundle 40 in order to almost equally mix the fluorescences emitted from them. The fiber bundle 40 is also configured so that the barycenters of the output intensities of fluorescences that are emitted via the partial fiber bundles 40-1, 40-2, and 40-3 almost coincide with the center of the effective exit region of the fiber bundle 40 at the exit end of the fiber bundle 40. The numbers of single fibers contained in the partial fiber bundles 40-1, 40-2, and 40-3 can be equal to each other, and can be adjusted in accordance with the emission intensities of the respective fluorescences so that the fluorescences emitted via the partial fiber bundles 40-1, 40-2, and 40-3 combine to become light of a desired color, e.g., white.

Referring to FIGS. 6 and 7, the exciting light beams emitted from the semiconductor lasers 10-1, 10-2, and 10-3 respectively strike the corresponding phosphor units 30-1, 30-2, and 30-3 via the single fibers 20-1, 20-2, and 20-3. The phosphor units 30-1, 30-2, and 30-3 respectively generate fluorescences of the red, blue, and green regions upon receiving exciting light beams exiting from the single fibers 20-1, 20-2, and 20-3. The fluorescences generated from the phosphor units 30-1, 30-2, and 30-3 exit as white illumination light 110 from the exit end of the fiber bundle 40 via the respective partial fiber bundles 40-1, 40-2, and 40-3.

Figure 8:
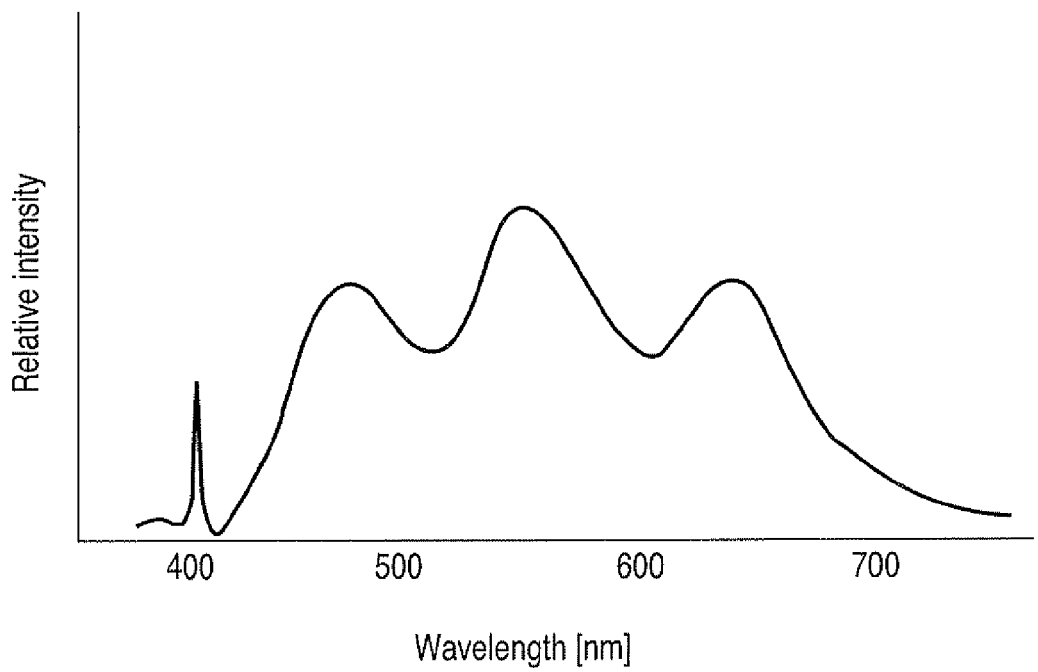
FIG. 8 is a graph showing the spectrum of illumination light exiting from the optical fiber lighting apparatus in FIG. 6.

In this embodiment, in selecting a phosphor, as shown in FIG. 8, a phosphor that generates fluorescence having a broader spectrum range than that in the second embodiment is selected. In this case, a transmission loss is preferably calculated in consideration of not only the peak of the fluorescence generated from each phosphor but also the lower and higher band ends of the spectrum. For this reason, a transmission loss is calculated throughout the visible light range in which ordinary human beings can see, i.e., the range of 400 nm to 700 nm, as well as the peak of the light. In other words, a desired RGB output ratio is preferably set in consideration of not only the R, G, and B regions but also the range from the red region to the violet region, which is the visible region. Referring to FIG. 3, the difference $\Delta\alpha$ between the maximum and minimum values of transmission losses is 0.2 dB/m, which is obtained by subtracting 0.05 dB/m (the transmission loss at 700 nm) from 0.25 dB/m (the transmission loss at 400 nm). The difference corresponds to 4.5%/m. As a consequence, when the range of the length of the fiber bundle 40, i.e., the difference between the maximum and minimum lengths of the fiber bundle 40, is set to 1.1 m or less, the allowable value $\Delta\lambda$ of the difference between the intensity changes of the spectra of the respective wavelength components can be set to 10% or less. That is, it suffices to set the range of the length of the fiber bundle 40 to 1.1 m or less with respect to $\Delta\lambda$ of 10%. Assume that there is a need to reduce a change in color appearance for medical applications and the like. In this case, if $\Delta\lambda$ is set to, for example, 5%, the range of the length of the fiber bundle 40 needs to be set to approximately 50 cm.

In addition, when color appearance adjustment is performed by using only the phosphor units 30-1, 30-2, and 30-3, it suffices to set the length of the fiber bundle 40 to 1.1 m and 0.55 m or less for $\Delta\lambda$ of 10% and 5%, respectively. That is, when color appearance adjustment is performed by using only the phosphor units 30-1, 30-2, and 30-3, the minimum value of the range of the length of the fiber bundle 40 is 0 m. For this reason, it suffices to set the maximum value to 1.1 m and 0.55 m for $\Delta\lambda$.

In this embodiment, the light guided by the fiber bundle 40 has peaks in its intensity spectrum. The difference $\Delta\alpha$ between the maximum and minimum values of light guide losses is the value obtained by subtracting the minimum value of light guide losses with respect to the light beams generated from the phosphor units 30-1, 30-2, and 30-3 and light guide losses with respect to the exciting light beams emitted from the semiconductor lasers 10-1, 10-2, and 10-3 from the maximum value of the light guide losses. If these light beams have a wavelength outside the visible light range, the light guide loss may be calculated based only on the light beams whose wavelength is within the visible light range.

As described above, according to this embodiment, it is possible to reduce the influence of a change in the length of the fiber bundle 40 on an RGB output ratio and provide a stable optical fiber lighting apparatus in which the color appearance of illumination light does not change in the wavelength range of the illumination light.

Fourth Embodiment

Figure 9:
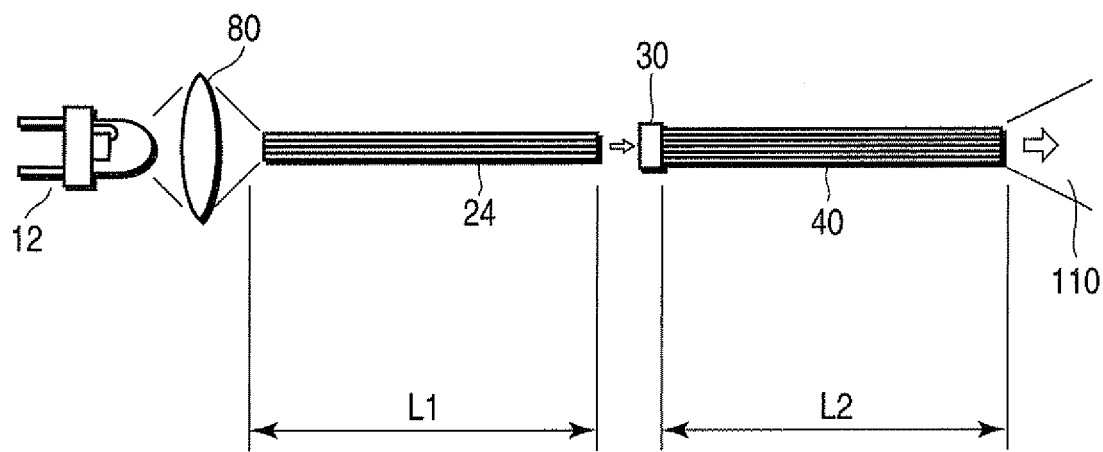
FIG. 9 is a schematic view of an optical fiber lighting apparatus according to the fourth embodiment of the present invention.

FIG. 9 shows an optical fiber lighting apparatus according to the fourth embodiment of the present invention. The optical fiber lighting apparatus of this embodiment has the same basic structure as that of the first embodiment except that the apparatus of the fourth embodiment includes an LED 12 that emits LED light as an exciting light source in place of the semiconductor laser 10, and a fiber bundle 24 comprising a bundle of single fibers as the first optical fiber in place of the single fiber 20. Using the LED 12 as an exciting light source can simultaneously achieve low cost and eye safety. In addition, this can simplify the system by eliminating the necessity of a feedback circuit for optical outputs. Furthermore, using the fiber bundle 24 as the first optical fiber that guides exciting light can efficiently guide LED light and apply it to a phosphor unit 30.

In this embodiment, the exciting light source comprises the lamp-type LED 12 having a dome lens. However, the embodiment is not limited to this. The exciting light source may comprise a current confinement type LED light source or SLD (Super Luminescent Diode) light source. Using a current confinement type LED light source or SLD light source can improve the coupling efficiency with an optical fiber as compared with general LED light. This can therefore improve the utilization efficiency of exciting light.

As described above, according to this embodiment, there can be provided a stable optical fiber lighting apparatus in which the color appearance of illumination light does not change in the wavelength range of the illumination light.

Although the embodiments of the present invention have been described with reference to the views of the accompanying drawing, the present invention is not limited to these embodiments. The embodiments can be variously modified and changed within the spirit and scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical fiber lighting apparatus comprising:
   an exciting light source that emits exciting light;
   a first optical fiber that guides the exciting light emitted from the exciting light source;
   a wavelength conversion unit that receives the exciting light exiting from the first optical fiber to generate wavelength-converted light having a wavelength different from that of the exciting light; and
   a second optical fiber that guides at least part of the wavelength-converted light generated by the wavelength conversion unit.

2. The apparatus according to claim 1, wherein light guided by the second optical fiber has a wide range of wavelengths, and a length of the second optical fiber is set on the basis of a light guide loss in a wavelength range of light guided by the second optical fiber.

3. The apparatus according to claim 1, wherein light guided by the second optical fiber has a wide range of wavelengths, and a length of the second optical fiber is determined so that a spectrum of light exiting from an exit end of the second optical fiber has a predetermined pattern corresponding to a desired RGB output ratio at the exit end.

4. The apparatus according to claim 1, wherein the exciting light source comprises a laser source that emits laser light, the first optical fiber comprises a single fiber that guides the laser light, and the second optical fiber comprises a fiber bundle comprising a bundle of single fibers.

5. The apparatus according to claim 1, wherein the exciting light source comprises an LED light source that emits LED light, the first optical fiber comprises a fiber bundle that comprises a bundle of single fibers and guides the LED light, and the second optical fiber comprises a fiber bundle comprising a bundle of single fibers.

6. The apparatus according to claim 2, wherein letting $\Delta\alpha$ [dB/m] be a difference between a maximum value and a minimum value of light guide losses due to the second optical fiber in a wavelength range of illumination light exiting from the second optical fiber and $\Delta\lambda$ [%] be an allowable value of a difference between intensity changes of spectra of the respective wavelength components in the wavelength range of the illumination light, a range of a length of the second optical fiber is not more than $\text{Lmax [m]} = \Delta\lambda/((1-10^{(-\Delta\alpha/10)}) \times 100)$.

7. The apparatus according to claim 4, wherein light guided by the second optical fiber is white light, the exciting light source comprises a blue semiconductor laser source having a peak at a wavelength of not more than 480 nm, and the wavelength conversion unit includes a phosphor that generates fluorescence having a peak at at least not less than 540 nm.

8. The apparatus according to claim 2, wherein light guided by the second optical fiber has peaks in an intensity spectrum of the light, and letting $\Delta\alpha$ [dB/m] be a difference between a maximum value and a minimum value of light guide losses at wavelengths at the peaks and $\Delta\lambda$ [%] be an allowable value of a difference between intensity changes of spectra of the respective wavelength components in the wavelength range of the illumination light, a range of a length of the second optical fiber is not more than $\text{Lmax [m]} = \Delta\lambda/((1-10^{(-\Delta\alpha/10)}) \times 100)$.

9. The apparatus according to claim 2, comprising exciting light sources that respectively emit exciting light beams, first optical fibers that respectively guide the exciting light beams emitted from the exciting light sources, and wavelength conversion units that respectively generate wavelength-converted light beams having different wavelengths upon receiving the exciting light beams exiting from the first optical fibers, and in which the second optical fiber guides at least parts of the wavelength-converted light beams generated by the wavelength conversion units, and letting $\Delta\alpha$ [dB/m] be a difference between a maximum value and a minimum value of light guide losses with respect to light beams generated by the wavelength conversion units and light guide losses with respect to exciting light beams emitted from the exciting light sources, and $\Delta\lambda$ [%] be an allowable value of a difference between intensity changes of spectra of the respective wavelength components in the wavelength range of the illumination light, a range of a length of the second optical fiber is not more than $\text{Lmax [m]} = \Delta\lambda/((1-10^{(-\Delta\alpha/10)}) \times 100)$.

* * * * *